(12) United States Patent
Haubrich et al.

(10) Patent No.: US 8,374,700 B2
(45) Date of Patent: Feb. 12, 2013

(54) ADJUSTABLE IMPEDANCE MATCHING CIRCUIT

(75) Inventors: Gregory J. Haubrich, Champlin, MN (US); Robert S. Wentink, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 756 days.

(21) Appl. No.: 12/533,551

(22) Filed: Jul. 31, 2009

(65) Prior Publication Data
US 2010/0030304 A1 Feb. 4, 2010

Related U.S. Application Data

(60) Provisional application No. 61/085,343, filed on Jul. 31, 2008.

(51) Int. Cl.
*A61N 1/00* (2006.01)
*H01Q 1/40* (2006.01)
(52) U.S. Cl. ............... 607/60; 607/30; 607/36; 343/873
(58) Field of Classification Search .................... 607/30, 607/36, 60; 343/873
See application file for complete search history.

(56) References Cited

U.S. PATENT DOCUMENTS

| | | | |
|---|---|---|---|
| 5,778,308 A | 7/1998 | Sroka et al. | |
| 6,456,256 B1* | 9/2002 | Amundson et al. | ........... 343/873 |
| 6,765,540 B2 | 7/2004 | Toncich | |
| 6,885,353 B2 | 4/2005 | Kurihara | |
| 7,047,076 B1 | 5/2006 | Li et al. | |
| 7,256,695 B2 | 8/2007 | Hamel et al. | |
| 7,409,245 B1 | 8/2008 | Larson et al. | |
| 2002/0123776 A1 | 9/2002 | Von Arx et al. | |
| 2008/0180345 A1 | 7/2008 | Larson et al. | |
| 2008/0288028 A1 | 11/2008 | Larson et al. | |

OTHER PUBLICATIONS

International Search Report for PCT/US2009/052410, Jan. 2009.

* cited by examiner

*Primary Examiner* — Nicole F Lavert
(74) *Attorney, Agent, or Firm* — Stephen W. Bauer; Michael J. Ostrom

(57) ABSTRACT

An implantable medical device with a medical module, an antenna, a transceiver and an impedance match circuit. The transceiver is operatively coupled to the antenna and the medical module and facilitates wireless transmission of data between the medical module and an external device. The impedance match circuit is operatively coupled between the transceiver and the antenna and has a plurality of predetermined selectable configurations, each providing a particular impedance matching characteristic.

11 Claims, 4 Drawing Sheets

ADJUSTABLE IMPEDANCE MATCHING CIRCUIT

RELATED APPLICATION

This application claims priority from provisional U.S. Patent Application No. 61/085,343, Haubrich, Adjustable Impedance Matching Circuit, filed Jul. 31, 2008.

FIELD

This disclosure relates to telemetry communication with implantable medical devices and, in particular, impedance matching to adapt such telemetry communications to the environment in which the implantable medical device is operating.

BACKGROUND

The use of wireless communications in implantable medical devices is well known in the art. Using both inductive and radio frequency communications, data and commands may be transmitted to an implantable medical device and telemetry data may be received from the implantable medical device. In a radio frequency application, the implantable medical device may utilize a relatively small, space-efficient antenna coupled to an internal transceiver to establish a communication link with an antenna of an external device positioned in proximity of the internal antenna.

The effective range and rate of radio frequency communication may depend in part on a degree to which the impedance of the antenna of the external device matches the impedance of the antenna of the internal device. The closer the impedance match, the clearer the signal between the two antennas may be and the greater the rate the communication may be. Beyond the impact of variance in the componentry utilized in wireless communications, the environment in which the implantable medical device operates may have an impact on the perceived impedance of the internal antenna.

For instance, U.S. Pat. No. 7,409,245, Larson et al., discloses a variable antenna matching network for an implantable antenna. Changes in the patient's body position, weight, composition or other factors may change the antenna efficiency and hinder communication. The disclosed circuit may automatically adjust a matching network for an implanted transceiver to dynamically maximize transmission and reception by controlling the selected value of a plurality of capacitors, inductors and resistors.

However, because of the premium placed on making implantable medical devices relatively small, many internal antennas are not tunable. As a result, manufacturers of implantable medical devices have traditionally made a compromise between maximizing wireless communication efficiency and range and keeping the internal volume of the implantable medical device small.

SUMMARY

Thus, while real-time tunable impedance matching circuits have been utilized to improve telemetry communication with implantable medical devices, such circuits typically expend a significant amount of implantable medical device resources including increasing the internal volume of the implantable medical device, expending computing power of the implantable medical device, and reducing the service life of a power source (for instance, a battery) of the implantable medical device.

In an embodiment, an impedance match circuit is provided for an implantable medical device which, instead of being tunable in real-time, has a plurality of predetermined selectable configurations. In one example, one of the predetermined configurations may correspond to the antenna operating in air, while another of the predetermined configurations may correspond to the antenna operating after implantation in a patient. Alternative configurations may also be provided for alternative circumstances. By establishing predetermined configurations, impedance matching may be provided which is smaller, simpler, and less wasteful of implantable medical device resources such as computing power and system power, among other benefits.

In an embodiment, an implantable medical device comprises a medical module, an antenna, a transceiver and an impedance match circuit. The transceiver is operatively coupled to the antenna and the medical module and facilitates wireless transmission of data between the medical module and an external device. The impedance match circuit is operatively coupled between the transceiver and the antenna and has a plurality of predetermined selectable configurations, each providing a particular impedance matching characteristic.

In an embodiment, a first configuration and a second configuration of the plurality of predetermined selectable configurations correspond to operating the antenna in air and implanted in a patient, respectively.

In an embodiment, the implantable medical device further comprises a memory module operatively coupled to the impedance match circuit, the memory module storing the first configuration and the second configuration.

In an embodiment, the first configuration and the second configuration are selectable by a command generated external to the implantable medical device.

In an embodiment, the antenna is configured to receive a wireless signal, wherein the transceiver is configured to identify the command contained within the wireless signal and wherein one of the first configuration and the second configuration is selected based on the command.

In an embodiment, the memory module stores a plurality of codes, each one of the plurality of codes being representative of one of the first configuration and the second configuration.

In an embodiment, one of the first configuration and the second configuration is selected based, at least in part, on a selection of one of the plurality of codes from a command generated external to the implantable medical device.

In an embodiment, the transceiver is configured to receive a selection of the one of the plurality of codes from a wireless signal.

In an embodiment, a method is disclosed for matching impedance with an impedance match circuit operatively coupled between an antenna and a transceiver of an implantable medical device, the impedance match circuit having a plurality of predetermined configurations, each individual one of the plurality of configurations providing a particular impedance matching characteristic. A first one of the plurality of predetermined configurations corresponding to a first environment in which the antenna is selected. Then the antenna is moved from the first environment to a second environment. A second one of the plurality of predetermined configurations corresponding to the second environment is selected.

In an embodiment, the implantable medical device further comprises a memory module, and the method further comprises the step, before the selecting a first one of the plurality of predetermined configurations step, of storing the first one and the second one of the plurality of predetermined configurations in the memory module.

In an embodiment, a computer readable medium is disclosed having computer executable instructions for performing a method for matching impedance with an impedance match circuit operatively coupled between an antenna and a transceiver of an implantable medical device, the impedance match circuit having a plurality of predetermined configurations, each individual one of the plurality of configurations providing a particular impedance matching characteristic. A first one of the plurality of predetermined configurations corresponding to a first environment in which the antenna is selected. Then the antenna is moved from the first environment to a second environment. A second one of the plurality of predetermined configurations corresponding to the second environment is selected.

DRAWINGS

DESCRIPTION

Provisional U.S. Patent Application No. 61/085,343, Haubrich, Adjustable Impedance Matching Circuit, filed Jul. 31, 2008, is herein incorporated by reference in its entirety.

Figure 1:
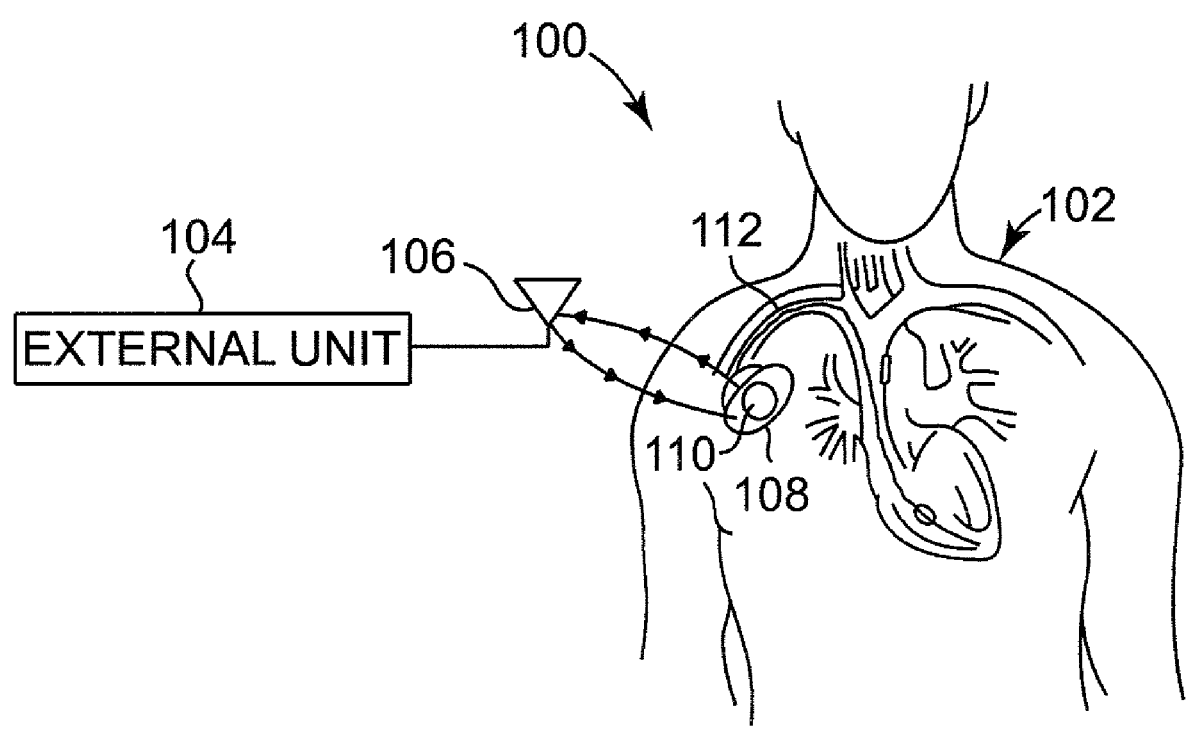
FIG. 1 is a schematic diagram illustrating one embodiment of a communication system for communicating medical data between an implantable medical device (implantable medical device) and an external unit.

FIG. 1 is a schematic diagram illustrating one embodiment of a communication system 100 for communication between an implantable medical device 108, which includes lead 112 and antenna 110, and external unit 104. In one embodiment, implantable medical device 108 is an implantable cardioverter-defibrillator, but the embodiments of the present invention are equally applicable to many types of medical devices, including both implantable medical devices and external medical devices. For example, implantable medical device 108 may provide electrical stimulation therapy (e.g., a combination at least one of pacing, defibrillation, cardioversion or cardiac resynchronization therapy). In other instances, implantable medical device 108 may provide electrical stimulation therapy to other regions of the body, e.g., a spine, brain, or the like. In yet another example, implantable medical device 108 may provide drug delivery therapy or other therapies in addition to or instead of electrical stimulation therapy.

In addition to or instead of providing therapy, implantable medical device 108 may be capable of sensing physiological events of the heart of patient 102 via electrodes of lead 112. Implantable medical device 108 may also sense one or more physiological or biological conditions of other regions of patient 102 via electrodes of lead 112 or other sensors on lead 112, within implantable medical device 108 or separate stand-alone sensors. Antenna 110 is used to communicate with external unit 104 and may be any suitable device capable of sending or receiving electromagnetic waves, including for example a surface mounted antenna, an inductor, or a half-wave strip.

External unit 104 is a device, such as a programmer or home monitor, capable of bi-directional communication with implantable medical device 108 via antenna 106. External unit 104 includes antenna 106, which may be any suitable type of radio frequency antenna capable of communicating in the desired radio frequency frequencies with implantable medical device 108, and may be located inside or outside of a housing of external unit 104.

Implantable medical device 108 includes an adjustable impedance matching circuit for impedance matching antenna 110 to a radio frequency transceiver within the device can of implantable medical device 108. By adjusting the impedance matching circuit between different predetermined impedances, operation of antenna may be increased. Moreover, providing the capability to adjust between different predetermined impedances allows better impedance matches to be achieved between antenna 110 and the transceiver of implantable medical device in different operating environments, e.g., prior to implantation (in air) and after implantation (in the body). Additionally, a variety of antennas 110 having different impedances may by used with a single radio frequency transceiver used in different implantable medical devices without having to use a separate impedance matching circuit for each of the variety of antennas. Therefore, both development times and costs are reduced while improving communication performance.

Figure 2:
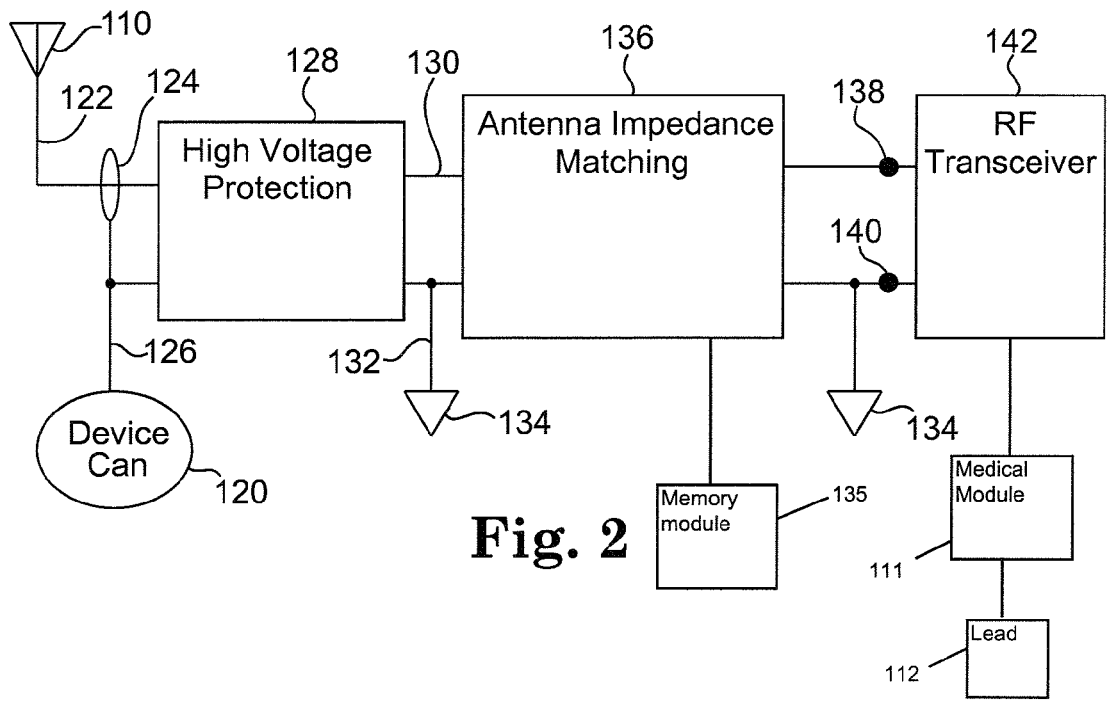
FIG. 2 is block diagram illustrating one embodiment of a portion of an implantable medical device circuit.

FIG. 2 is block diagram illustrating one embodiment of a portion of an implantable medical device circuit. The circuit includes antenna 110, the implantable medical device 108 device can 120, a high voltage protection circuit 128, an antenna impedance matching circuit 136, and a radio frequency transceiver 142. Antenna 110 is electrically coupled to an input of high voltage protection circuit 128 through signal path 122. Signal path 122 passes through a feed through 124 of device can 120. Feed through 124 is electrically coupled to device can 120 and a second input of high voltage transceiver 128 through signal path 126.

Medical module 111 is coupled to lead 112 and provides sensing and/or therapy functions consistent with those commonly provided in implantable medical devices such as pacemakers, cardioverters/defibrillators, neurological stimulators and drug infusion devices. In various embodiments, medical module 111 is operatively coupled to radio frequency transceiver 142 and receives instructions and transmits data to external unit 104 by way of radio frequency transceiver 142. In certain embodiments, medical module 111 is directly coupled to radio frequency transceiver 142. In alternative embodiments various electronics modules commonly known in the art are coupled between radio frequency transceiver 142 and medical module 111 in order to facilitate communication between radio frequency transceiver 142 and medical module 111, including controllers and data storage.

A first output of high voltage protection circuit 128 is electrically coupled to a first input of antenna impedance matching circuit 136 through signal path 130. A second output of high voltage protection circuit 128 is electrically coupled to a second input of antenna impedance matching circuit 136 and to a common or ground 134 through signal path 132. A first output of antenna impedance matching circuit 136 is electrically coupled to a first input of radio frequency transceiver 142 through signal path or node 138. A second output of antenna impedance matching circuit 136 is electrically coupled to a second input of radio frequency transceiver 142 and to common or ground 134 through signal path or node 140.

Antenna 110 receives radio frequency signals from external unit 104 (FIG. 1) and transmits radio frequency signals to external unit 104. Feed through 124 is hermetically sealed such that circuits within device can 120 are protected when implanted within a patient. In one embodiment, device can 120 includes titanium or other suitable material. High voltage protection circuit 128, antenna impedance matching circuit 136, radio frequency transceiver 142, and other implantable medical device 108 circuitry (not shown) is enclosed within device can 120.

High voltage protection circuit 128 protects implantable medical device 108 circuitry from high voltages on signal path 122 and/or 126. In one embodiment, high voltage protection circuit 128 includes a radio frequency limiter to limit the amount of radio frequency energy that is allowed to pass through to antenna impedance matching circuit 136. As such, protection circuit 128 protects implantable medical device 108 circuitry from radiation emitted from, for example, two-way radios, magnetic resonance imaging (MRI) machines, or other radiation to which a patient may be exposed.

Antenna impedance matching circuit 136 matches the impedance of antenna 110 to the impedance of radio frequency transceiver 142. In one embodiment, radio frequency transceiver 142 has a receiver input impedance of 50 ohms and a transmitter output impedance of 50 ohms between nodes 138 and 140, and antenna 110 has an impedance less than 50 ohms. Antenna impedance matching circuit 136 matches the lower impedance of antenna 110 to the higher impedance of radio frequency transceiver 142. Antenna impedance matching circuit 136 can be adjusted to match the impedance of antenna 110 to the impedance (or as close to as possible) radio frequency transceiver 142 in different operating environments. For example, antenna impedance matching circuit 136 may have one predetermined configuration corresponding to the antenna operating in air and another predetermined configuration corresponding to the antenna operating after implantation in a patient. Antenna impedance matching circuit 136 can also be adjusted to match different antennas 110 having different impedances to radio frequency transceiver 142 in addition to or instead of adjusting the impedance in different operating environments. In this way, multiple implantable medical devices 108 having different designs and antenna designs having different impedances can use the same antenna impedance matching circuit 136 and radio frequency transceiver 142. Therefore, a unique antenna impedance matching circuit 136 and/or radio frequency transceiver is not needed for each individual implantable medical device 108 design or antenna design.

In various embodiments, impedance matching circuit 136 is coupled to memory module 135. In such embodiments, codes to configure impedance matching circuit 136 may be stored in memory module 135 and transmitted to impedance matching circuit 136 at appropriate times. The appropriate times may be determined on the basis of conditions sensed by medical module 111. For example, antenna impedance matching circuit 136 may be configured to switch from the predetermined configuration corresponding to the antenna operating in air to the predetermined configuration corresponding to the antenna operating upon detecting a cardiac signal via one of the leads. Detection of a cardiac signal may indicate that implantable medical device 108 is implanted within patient 112. In alternative embodiments, commands may be transmitted from external unit 104 by way of antenna 110 and identified by radio frequency transceiver 142 or a coupled controller which are configured to identify the command and cause the code to be transmitted from memory module 135 to impedance matching circuit 136 to adjust the impedance. The command may, for example, be transmitted by a programmer after implantation.

On the basis of the codes transmitted to impedance matching circuit 136, impedance matching circuit 136 may be reconfigured in a manner described in detail below. In certain embodiments, memory module 135 may also be coupled to radio frequency transceiver 142 and may be loaded with newly transmitted codes. In particular, in various embodiments, memory module 135 may be pre-stored with derived codes corresponding to predetermined selectable configurations. In certain embodiments, such configurations relate to implantable medical device 108 operating outside of patient 102, and implantable medical device operating implanted within patient 102. In order to derive such codes, antenna 110 may be replaced by test loads simulating the various conditions in which implantable medical device 108 may operate. In alternative embodiments, the predetermined selectable configurations relate to other conditions in which implantable medical device 108 may be operating, and may be obtained either on the basis of simulated test loads or through configurations predetermined in ways related to devices of the same type as implantable medical device 108 but not necessarily to implantable medical device 108 individually.

In one embodiment, antenna impedance matching circuit 136 includes one inductor and one variable capacitor, such as a veractor or switched capacitor, to impedance match antenna 110 to radio frequency transceiver 142. In various alternative embodiments, antenna impedance matching circuit 136 includes various combinations of inductors and variable capacitors in a selectable configuration. Such alternative embodiments may include embodiments with no inductors which rely only on capacitors, and embodiments with no capacitors which rely only on inductors.

Radio frequency transceiver 142 includes a receiver for receiving radio frequency signals transmitted from external unit 104 via antenna 106 to antenna 110. Radio frequency transceiver 142 also includes a transmitter for transmitting radio frequency signals to external unit 104 via antenna 110. Transceiver 142 is electrically coupled to additional circuitry (not shown) within implantable medical device 108. The additional circuitry provides therapies and/or senses physiological events of the patient.

In one embodiment, the output power of radio frequency transceiver 142 is checked periodically (or often enough to be nearly continuous). The output power is greatest when antenna 110 is properly matched to radio frequency transceiver 142. In other embodiments, the received signal strength is maximized to properly impedance match antenna 110 to radio frequency transceiver 142 maximizing the output power or received signal strength to compensate for antenna feedpoint impedance variations as can occur (i.e. a hand-held instrument or an implant prior and after implant).

Figure 3:
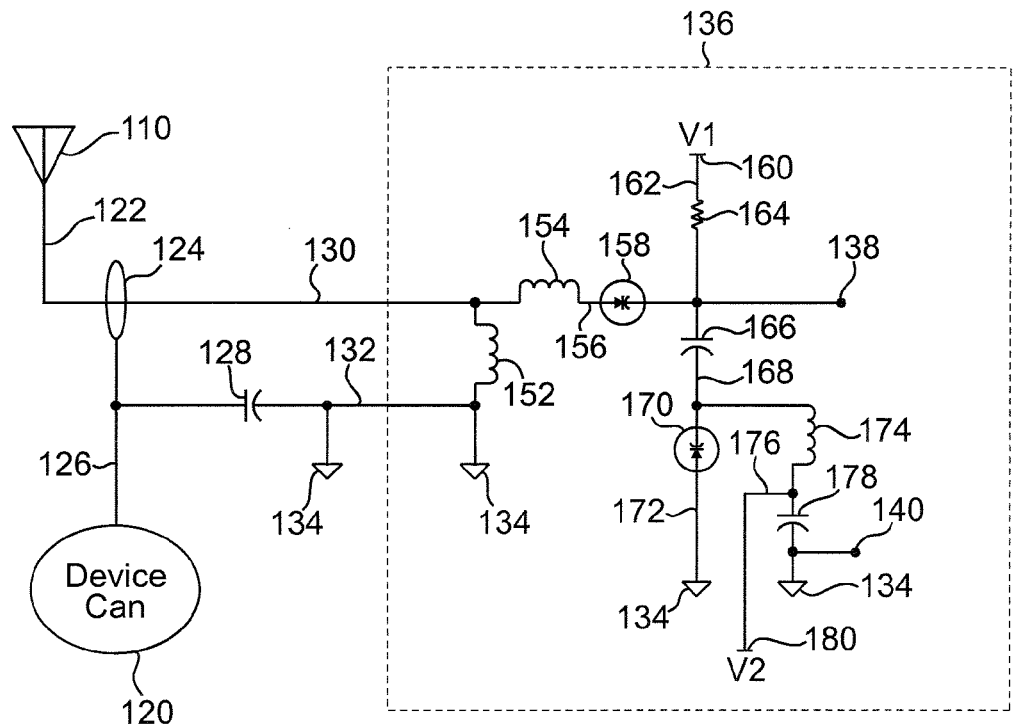
FIG. 3 is an electrical schematic diagram illustrating one embodiment of a portion of an implantable medical device circuit.

FIG. 3 is an electrical schematic diagram illustrating one embodiment of a portion of an implantable medical device circuit. The circuit includes antenna 110, device can 120, capacitor 128 and antenna impedance matching circuit 136. Antenna impedance matching circuit 136 includes capacitors 166 and 178, inductors 152, 154, and 174, varactors 158 and 170, and resistor 164. Antenna 110 is electrically coupled to one side of inductor 152 and one side of inductor 154 through signal paths 122 and 130. Signal path 122 passes through a feed through 124 of device can 120 and becomes signal path 130. Feed through 124 is electrically coupled to device can 120 and one side of capacitor 128 through signal path 126. The other side of capacitor 128 is electrically coupled to common or ground 134 and the other side of inductor 152 through signal path 132.

The other side of inductor 154 is electrically coupled to the anode of varactor 158 through signal path 156. The cathode of varactor 158 is electrically coupled to one side of resistor 164 and one side of capacitor 166 through signal path or node 138. The other side of resistor 164 is electrically coupled to a first voltage source (V1) 160 through signal path 162. The other side of capacitor 166 is electrically coupled to the cathode of varactor 170 and one side of inductor 174 through signal path 168. The anode of varactor 170 is electrically coupled to common or ground 134 through signal path 172. The other side of inductor 174 is electrically coupled to a second voltage source (V2) 180 and one side of capacitor 178 through signal path 176. The other side of capacitor 178 is electrically coupled to common or ground 134 through signal path or node 140.

Capacitor 128 provides high voltage protection for impedance matching circuit 136 and the radio frequency transceiver. In other embodiments, capacitor 128 is replaced with other suitable components for providing high voltage protection and/or for providing a radio frequency limiter. In one embodiment, inductors 152, 154, and 174 are off chip, and resistor 164, capacitors 166 and 178, and varactors 158 and 170 are on chip. Resistor 164 decouples first voltage source 160 from the radio frequency signal on signal path 138.

Varactors 158 and 170 each provide a variable capacitance for impedance matching antenna 110 to radio frequency transceiver 142, which is coupled to nodes 138 and 140. First voltage 160 and second voltage 180 are adjusted to adjust the capacitance of varactors 158 and 170. In one embodiment, first voltage 160 and second voltage 180 are provided by digital to analog converters (DACs). First voltage 160 and second voltage 180 can be adjusted once at factory calibration, adjusted in response to a command from external unit 104, and/or automatically adjusted to impedance match antenna 110 to radio frequency transceiver 142 for optimal performance.

Figure 4:
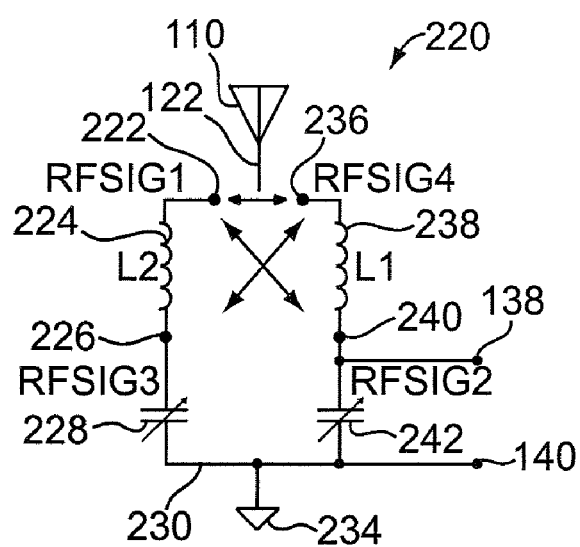
FIG. 4 is an electrical schematic diagram illustrating one embodiment of an antenna impedance matching circuit including a selectable topology.

FIG. 4 is an electrical schematic diagram illustrating one embodiment of an antenna impedance matching circuit 220 including a selectable topology. In one embodiment, antenna impedance matching circuit 220 is used in place of antenna impedance matching circuit 136 previously described and illustrated with reference to FIG. 2. Antenna impedance matching circuit 220 includes inductors 224 (L2) and 238 (L1) and tunable capacitors 228 and 242. In an embodiment, inductor 224 is 18 nanohenrys and inductor 238 is 10 nanohenrys. In an embodiment, tunable capacitors 228 and 242 have a range from 0.25 picoFarads to 25.0 picoFarads. In various alternative embodiments, the values of inductors 224 and 238 and of tunable capacitors 228 and 242 may vary as needed. In particular, inductors 224, 238 may be selected based on characteristics of antenna 110 and transceiver 142, while tunable capacitors 228, 242 may have a lower value as close to 0.0 Farads as can be achieved and an upper value based on characteristics of antenna 100 and transceiver 142. In various embodiments, tunable capacitors 228, 242 are formed on a common die with RFSIG1 signal path or node 222 is electrically coupled to one side of inductor 224. The other side of inductor 224 is electrically coupled to one side of tunable capacitor 228 through RFSIG3 signal path or node 226. The other side of tunable capacitor 228 is electrically coupled to a common or ground 234, one side of tunable capacitor 242, and node 140 through signal path 230. The other side of tunable capacitor 242 is electrically coupled one side of inductor 238 and node 138 through RFSIG2 signal path or node 240. The other side of inductor 238 is electrically coupled to RFSIG4 signal path or node 236.

In one embodiment, inductors 224 and 238 and tunable capacitors 228 and 242 are arranged into a topology based on selection chart 200 previously described and illustrated with reference to FIG. 5. In one embodiment, nodes 222, 226, 236, and 240 include pads accessible to the user for coupling antenna 110 and for coupling jumpers between the nodes for selecting the topology. As such the topologies which are illustrated in FIGS. 6A-6D are preselected configurations of impedance match circuit 136 of one embodiment. However, alternative jumper configurations may be selected between and among nodes 222, 226, 236 and 240 to create alternative topologies with alternative characteristics. Such alternative characteristics may be plotted on chart 200 of FIG. 5 and incorporated into decisions related to configuring impedance matching circuit 136 for various antennas 110 and transceivers 142, and the various embodiments in which antenna 110 operates.

Tunable capacitors 228 and 242 are adjusted in the selected topology to impedance match antenna 110 to the radio frequency transceiver, which is coupled to nodes 138 and 140. In one embodiment, each tunable capacitor 228 and 242 is a binary weighted switched capacitor bank, a linear weighted switched capacitor bank, or another suitable tunable capacitor that can be tuned digitally. Tunable capacitors 228 and 242 are set using a search, sweep, or other suitable method to match the impedance of antenna 110 to the radio frequency transceiver in the selected topology.

Figure 5:
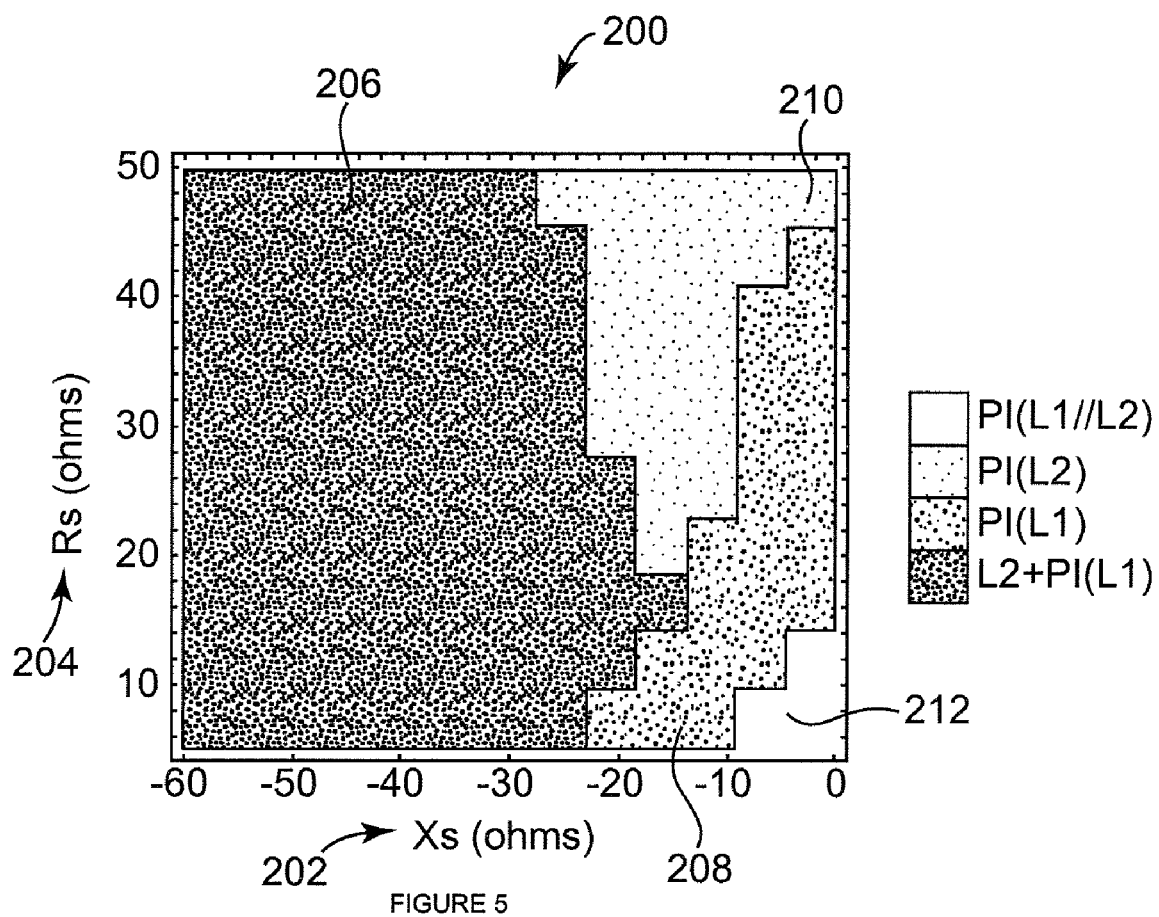
FIG. 5 is one embodiment of a selection chart for selecting an antenna impedance matching circuit topology.
Figure 6A:
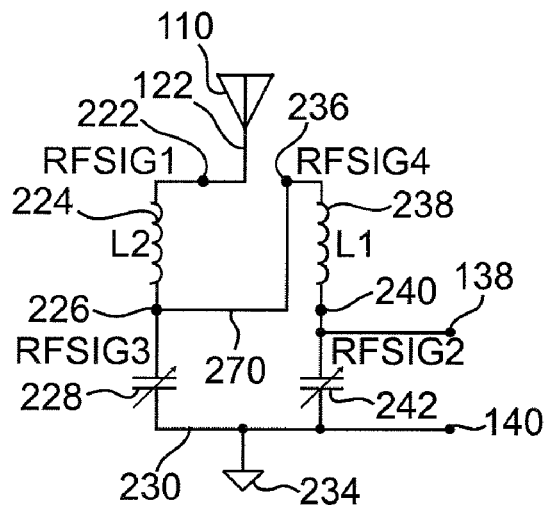
FIG. 6A is an electrical schematic diagram illustrating one embodiment of the antenna impedance matching circuit in a first topology.
Figure 6B:
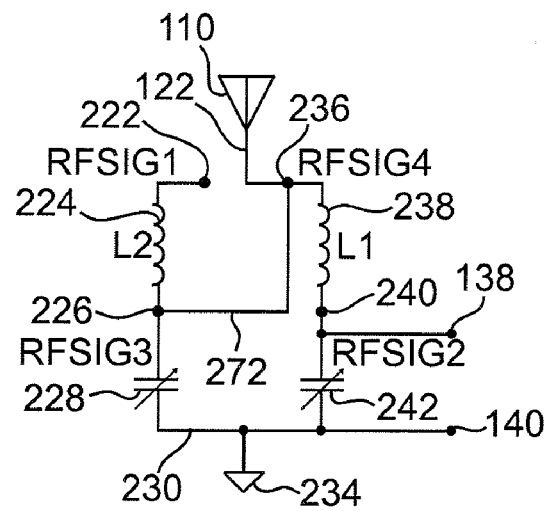
FIG. 6B is an electrical schematic diagram illustrating one embodiment of the antenna impedance matching circuit in a second topology.
Figure 6C:
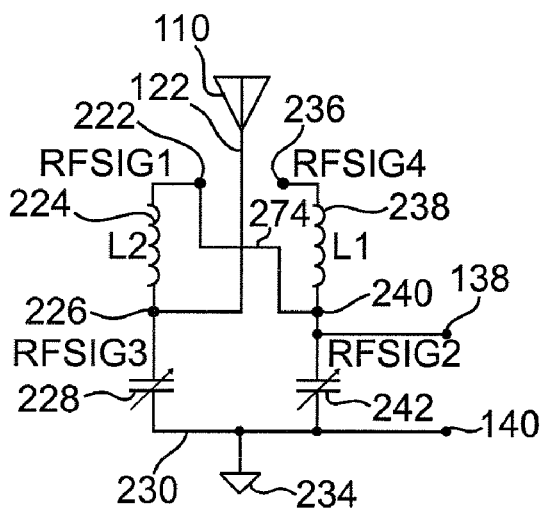
FIG. 6C is an electrical schematic diagram illustrating one embodiment of the antenna impedance matching circuit in a third topology.
Figure 6D:
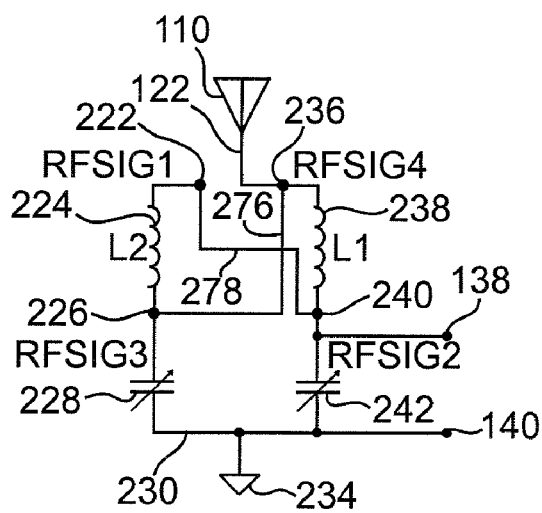
FIG. 6D is an electrical schematic diagram illustrating one embodiment of the antenna impedance matching circuit in a fourth topology.

FIG. 5 is one embodiment of a selection chart 200 for selecting an antenna impedance matching circuit topology. Selection chart 200 is used in combination with an antenna impedance matching circuit 220 that will be described below with reference to FIG. 4. Selection chart 200 includes reactance (Xs) in ohms on x-axis 202 and resistance (Rs) in ohms on y-axis 204. In this embodiment, the antenna resistance is between 5 ohms and 50 ohms, and the antenna reactance is between −60 ohms and 0 ohms. A first topology for impedance values within the range indicated at 206 is L2+PI(L1), where L1 is a first inductor and L2 is a second inductor. The first topology is illustrated in FIG. 6A below. A second topology for impedance values within the range indicated at 208 is PI(L1) and is illustrated in FIG. 6B below. A third topology for impedance values within the range indicated at 210 is PI(L2) and is illustrated in FIG. 6C below. A fourth topology for impedance values within the range indicated at 212 is PI(L1//L2) and is illustrated in FIG. 6D below.

For example, in one embodiment for an antenna impedance of 20-j40 ohms, the first topology L2+PI(L1) is selected. For an antenna impedance of 30-j5 ohms, the second topology PI(L1) is selected. For an antenna impedance of 40-j15 ohms, the third topology PI(L2) is selected. For an antenna impedance of 5-j5 ohms, the fourth topology PI(L1//L2) is selected.

Antenna impedance matching circuit 220 is configured in one of a first, second, third, and fourth topology based on selection chart 200 previously described and illustrated with reference to FIG. 4. The following FIGS. 6A-6D illustrate the first topology (i.e., L2+PI(L1)), the second topology (i.e., PI(L1)), the third topology (i.e., PI(L2)), and the fourth topology (i.e., PI(L1//L2)).

FIG. 6A is an electrical schematic diagram illustrating one embodiment of antenna impedance matching circuit 220 in the first topology (i.e., L2+PI(L1)). In this embodiment, antenna 110 is electrically coupled to RFSIG1 node 222 through signal path 122. RFSIG3 node 226 is electrically coupled to RFSIG4 node 236 through signal path 270. Tunable capacitors 228 and 242 are then tuned to match the impedance of antenna 110 to the radio frequency transceiver.

FIG. 6B is an electrical schematic diagram illustrating one embodiment of antenna impedance matching circuit 220 in the second topology (i.e., PI(L1)). In this embodiment, antenna 110 is electrically coupled to RFSIG4 node 236 through signal path 122. RFSIG4 node 236 is electrically coupled to RFSIG3 node 226 through signal path 272. Tunable capacitors 228 and 242 are then tuned to match the impedance of antenna 110 to the radio frequency transceiver.

FIG. 6C is an electrical schematic diagram illustrating one embodiment of antenna impedance matching circuit 220 in the third topology (i.e., PI(L2)). In this embodiment, antenna 110 is electrically coupled to RFSIG3 node 226 through signal path 122. RFSIG1 node 222 is electrically coupled to RFSIG2 node 240 through signal path 274. Tunable capacitors 228 and 242 are then tuned to match the impedance of antenna 110 to the radio frequency transceiver.

FIG. 6D is an electrical schematic diagram illustrating one embodiment of antenna impedance matching circuit 220 in the fourth topology (i.e., PI(L1//L2)). In this embodiment, antenna 110 is electrically coupled to RFSIG4 node 236. RFSIG4 node 236 is electrically coupled to RFSIG3 node 226 through signal path 276. RFSIG1 node 222 is electrically coupled to RFSIG2 node 240 through signal path 278. Tunable capacitors 228 and 242 are then tuned to match the impedance of antenna 110 to the radio frequency transceiver.

Embodiments provide an adjustable impedance matching circuit for matching the impedance of an implantable medical device telemetry antenna to a radio frequency transceiver of the implantable medical device. By adjusting the impedance matching circuit, the impedance of the antenna may be matched more closely to the impedance of the radio frequency transceiver of implantable medical device in different operating environments. For example, the antenna impedance matching circuit may have one predetermined configuration corresponding to the antenna operating in air and another predetermined configuration corresponding to the antenna operating after implantation in a patient. Alternatively or additionally, by adjusting the impedance matching circuit based on the selected telemetry antenna, a variety of telemetry antenna designs can be used with a single impedance matching circuit and radio frequency transceiver. Therefore, a different impedance matching circuit need not be designed for each telemetry antenna design, thereby saving development time and reducing costs.

Although the present invention has been described with reference to preferred embodiments, workers skilled in the art will recognize that changes can be made in form and detail without departing from the spirit and scope of the present invention.

What is claimed is:

1. An implantable medical device, comprising:
   a medical module;
   an antenna;
   a transceiver operatively coupled to said antenna and said medical module and facilitating wireless transmission of data between said medical module and an external device; and
   an impedance match circuit operatively coupled between said transceiver and said antenna, said impedance match circuit having a plurality of predetermined selectable configurations, each individual one of the plurality of configurations providing a particular impedance matching characteristic.

2. The implantable medical device of claim 1 wherein a first configuration and a second configuration of said plurality of predetermined selectable configurations correspond to operating said antenna in air and implanted in a patient, respectively.

3. The implantable medical device of claim 2 further comprising a memory module operatively coupled to said impedance match circuit, said memory module storing said first configuration and said second configuration.

4. The implantable medical device of claim 3 wherein said first configuration and said second configuration are selectable by a command generated external to said implantable medical device.

5. The implantable medical device of claim 4 wherein said antenna is configured to receive a wireless signal, wherein the transceiver is configured to identify said command contained within said wireless signal and wherein one of said first configuration and said second configuration is selected based on said command.

6. The implantable medical device of claim 3 wherein said memory module stores a plurality of codes, each one of said plurality of codes being representative of one of said first configuration and said second configuration.

7. The implantable medical device of claim 6 wherein one of said first configuration and said second configuration is selected based, at least in part, on a selection of one of said plurality of codes from a command generated external to said implantable medical device.

8. The implantable medical device of claim 7 wherein said transceiver is configured to receive a selection of said one of said plurality of codes from a wireless signal.

9. An implantable medical device, comprising:
   a medical module;
   an antenna;
   transceiver means operatively coupled to said antenna and said medical module for facilitating wireless transmission of data between said medical module and an external device; and
   impedance match means operatively coupled between said transceiver means and said antenna, said impedance match means for providing a plurality of predetermined selectable configurations, each individual one of the plurality of configurations providing a particular impedance matching characteristic.

10. The implantable medical device of claim 9 wherein a first configuration and a second configuration of said plurality of predetermined selectable configurations correspond to operating said antenna in air and implanted in a patient, respectively.

11. The implantable medical device of claim 10 further comprising memory means operatively coupled to said impedance match means, said memory means for storing said first configuration and said second configuration.

* * * * *